United States Patent [19]
Davis et al.

[11] Patent Number: 5,984,908
[45] Date of Patent: Nov. 16, 1999

[54] VENOUS RETURN CATHETER HAVING INTEGRAL SUPPORT MEMBER

[75] Inventors: Albert Davis, Richardson; Wendel Lloyd, Dallas; Christina Draper, Dallas; Mitta Suresh, Dallas; David Hernon; Richard C. Bryant, both of Richardson, all of Tex.

[73] Assignee: Chase Medical Inc, Richardson, Tex.

[21] Appl. No.: 08/838,802

[22] Filed: Apr. 10, 1997

[51] Int. Cl.$^6$ .................................................. A61M 25/00
[52] U.S. Cl. ........................... 604/282; 604/280; 604/264
[58] Field of Search .................... 604/19, 48, 52, 604/53, 102, 256, 264, 280, 282, 108, 109, 40, 42, 164

[56] References Cited

U.S. PATENT DOCUMENTS

| | | | |
|---|---|---|---|
| 3,674,033 | 7/1972 | Powers | 128/350 R |
| 4,129,129 | 12/1978 | Amrine | 128/214 |
| 4,402,684 | 9/1983 | Jessup | 604/264 |
| 4,596,548 | 6/1986 | DeVries et al. | 604/4 |
| 4,639,252 | 1/1987 | Kelly et al. | 604/282 |
| 4,680,029 | 7/1987 | Ranford et al. | 604/280 |
| 4,787,882 | 11/1988 | Claren | 604/4 |
| 4,804,365 | 2/1989 | Fitzie et al. | 604/4 |
| 4,808,158 | 2/1989 | Kreuger et al. | 604/49 |
| 4,863,441 | 9/1989 | Lindsay et al. | 604/280 |
| 5,041,084 | 8/1991 | DeVries et al. | 604/43 |
| 5,074,849 | 12/1991 | Sachse | 604/280 |
| 5,269,752 | 12/1993 | Bennett | 604/28 |
| 5,279,596 | 1/1994 | Castaneda et al. | 604/282 |
| 5,300,022 | 4/1994 | Klapper et al. | 604/35 |
| 5,314,418 | 5/1994 | Takano et al. | 604/282 |
| 5,324,253 | 6/1994 | McRea et al. | 604/282 |
| 5,334,169 | 8/1994 | Brown et al. | 604/282 |
| 5,336,191 | 8/1994 | Davis et al. | 604/165 |
| 5,342,325 | 8/1994 | Lun et al. | 604/272 |
| 5,344,399 | 9/1994 | DeVries | 604/96 |
| 5,356,388 | 10/1994 | Sepetka et al. | 604/164 |

(List continued on next page.)

OTHER PUBLICATIONS

Sarns Product Brochure, Two Stage Venous Return Catheter Part No. 12340.
Sarns Product Brochure, Wire Reinforced Venous Return Catheters Part No. 14032, 36, 40.
Sarns Product Brochure, Wire Reinforced Two Stage Venous Return Catheter Part No. 14992.
Medtronic Product Brochure, VC2 Atrial–Caval Cannulae.
Medtronic Product Brochure, TAC2 Two–stage, Atrial Caval Cannulae.

*Primary Examiner*—Corrine M. McDermott
*Assistant Examiner*—Cris L. Rodriguez
*Attorney, Agent, or Firm*—Robert C. Klinger; Neil Gershon

[57] ABSTRACT

A venous return catheter (30, 56, 60, 70) and method of use therefor having a semi-rigid support member (32) extending within a lumen (42) to prevent kinking thereof during insertion and use. The tubular walls of the catheter body (40,72) are sufficiently thin and flexible to provide maneuverability and allow clamping of the lumen (42) during use, but which outer diameter is sufficiently small and thus requires a smaller and less traumatic incision in the right atrium. The catheter is provided with a plurality of openings (34) along a length proximate the distal end of the catheter, and may have a second set of openings (74) in a two-stage catheter (70). The semi-rigid support member (32) is fixedly or selectively secured at a central location of the distal tip 44 free of the openings (34), but is free at the proximal end of the catheter to provide maneuverability. The semi-rigid support member may have a plurality of radially extending support members (57) to provide additional support. The catheter may also have a linear support member (62) integrally defined in the body wall (40) to prevent kinking but allow clamping.

13 Claims, 6 Drawing Sheets

U.S. PATENT DOCUMENTS

| | | | |
|---|---|---|---|
| 5,358,493 | 10/1994 | Schweich, Jr. et al. | 604/264 |
| 5,364,357 | 11/1994 | Aase | 604/96 |
| 5,401,244 | 3/1995 | Boykin et al. | 604/53 |
| 5,407,435 | 4/1995 | Sachse | 604/170 |
| 5,423,764 | 6/1995 | Fry | 604/187 |
| 5,441,484 | 8/1995 | Atkinson et al. | 604/96 |
| 5,443,448 | 8/1995 | DeVries | 604/96 |
| 5,449,343 | 9/1995 | Samson et al. | 604/96 |
| 5,460,608 | 10/1995 | Lodin et al. | 604/96 |
| 5,462,523 | 10/1995 | Samson et al. | 604/30 |
| 5,466,225 | 11/1995 | Davis et al. | 604/165 |
| 5,569,219 | 10/1996 | Hakki et al. | 604/282 |
| 5,571,091 | 11/1996 | Davis et al. | 604/165 |
| 5,593,394 | 1/1997 | Kanesaka et al. | 604/282 |
| 5,599,325 | 2/1997 | Ju et al. | 604/282 |
| 5,605,162 | 2/1997 | Mirzaee et al. | 128/772 |
| 5,607,394 | 3/1997 | Andersen et al. | 604/102 |
| 5,634,895 | 6/1997 | Igo et al. | 604/21 |
| 5,653,696 | 8/1997 | Shiber | 604/267 |
| 5,658,251 | 8/1997 | Ressemann et al. | 604/102 |
| 5,662,607 | 9/1997 | Booth et al. | 604/96 |
| 5,674,197 | 10/1997 | van Muiden et al. | 604/95 |
| 5,702,372 | 12/1997 | Nelson | 604/264 |

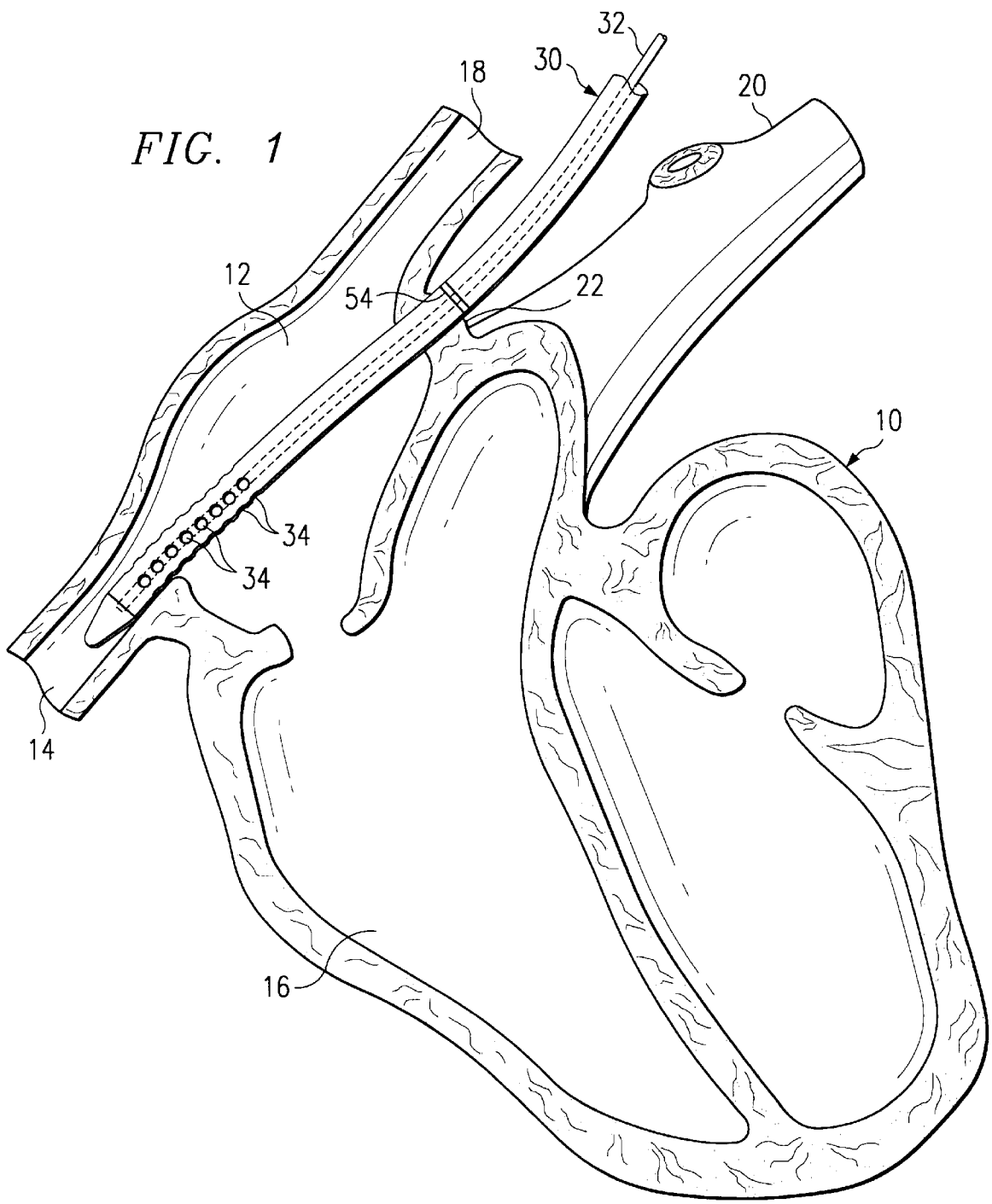

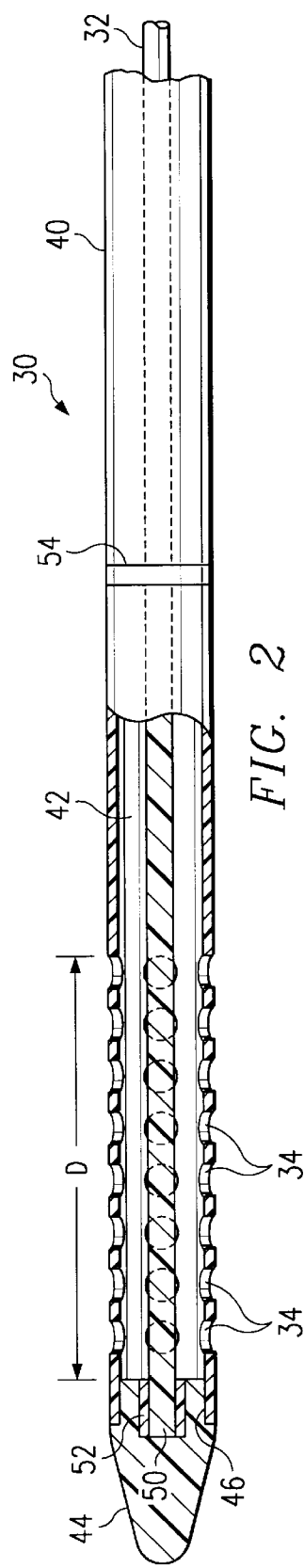
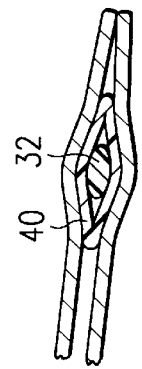
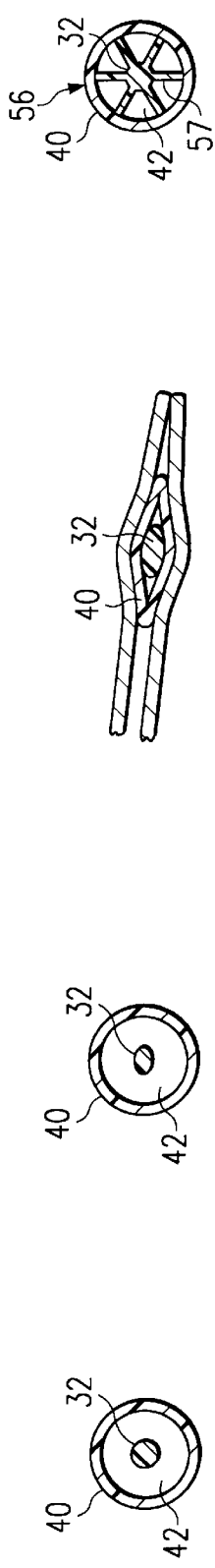
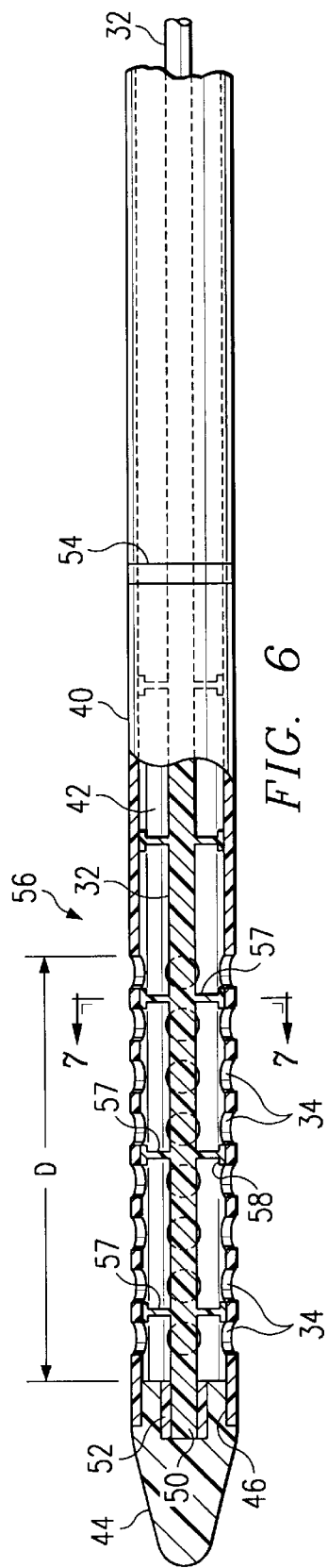

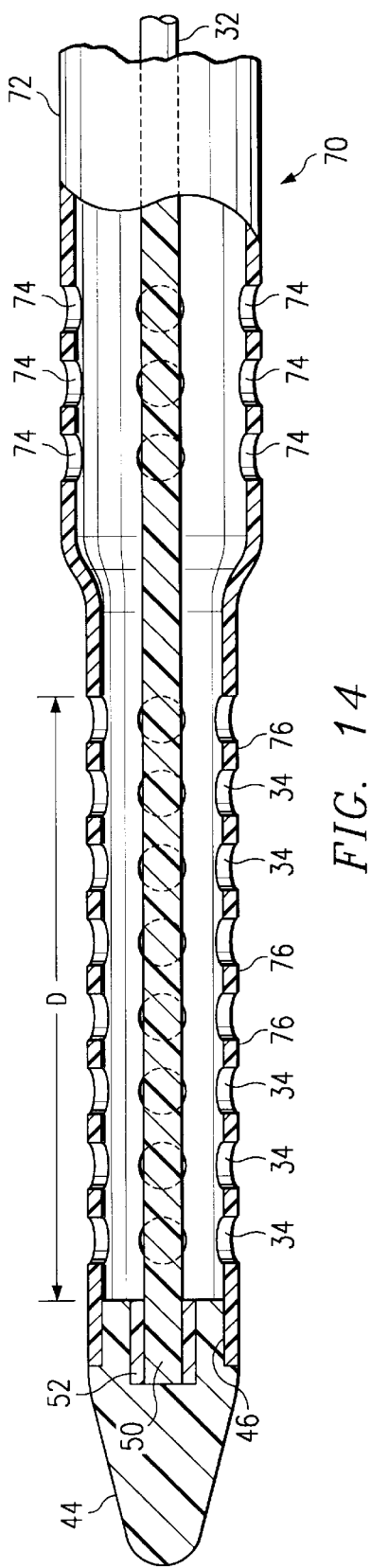
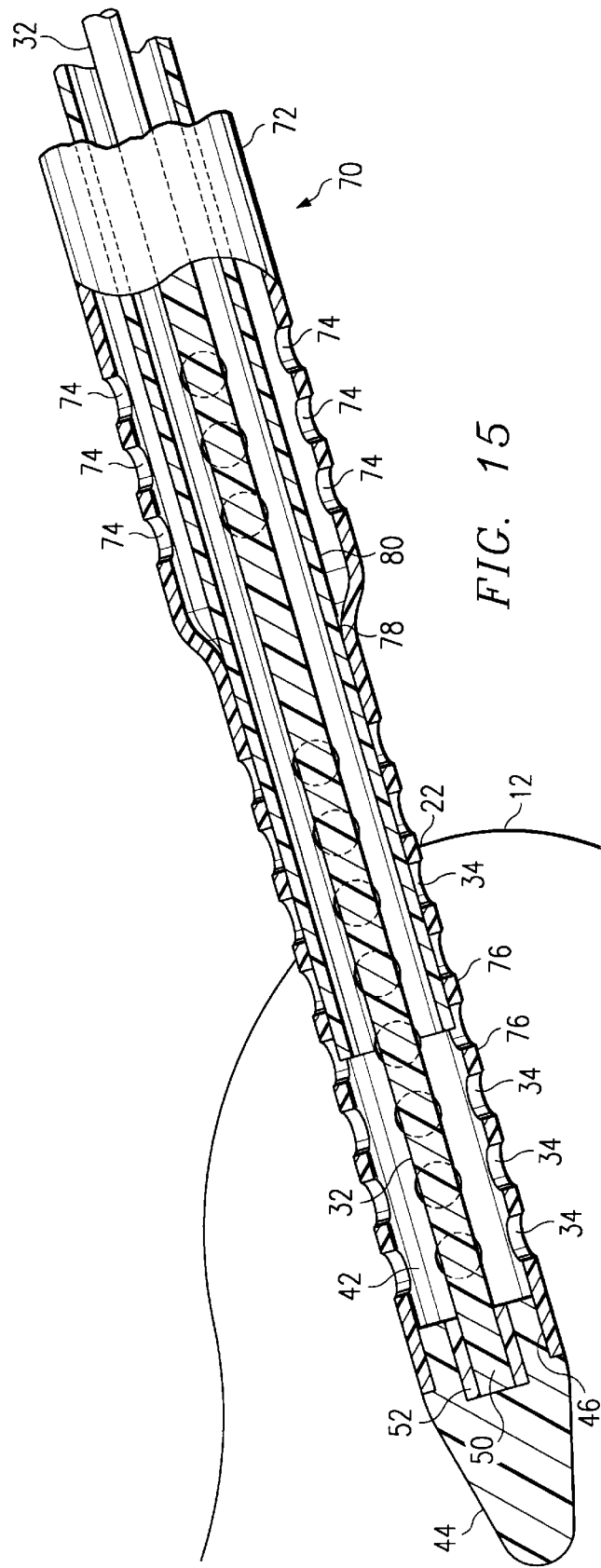
FIG. 14
FIG. 15

VENOUS RETURN CATHETER HAVING INTEGRAL SUPPORT MEMBER

FIELD OF THE INVENTION

The present invention is generally related to cardiac catheters, and more specifically to venous return catheters used to siphon blood from the right atrium of the heart during open heart surgery.

BACKGROUND OF THE INVENTION

Use of catheters to administer fluids into and drain fluids out of the body has been a standard practice in medical procedures for years. Many such catheters are available and used as part of an extracorporeal circuit during open heart procedures.

In a typical open heart procedure, blood is bypassed from the heart and lungs to a heart lung machine which, in combination with an oxygenator, pumps and oxygenates the blood passing through the extracorporeal circuit. When bypassing the heart, blood is siphoned away from the right atrium using a venous return (suction) catheter, oxygenated and returned to the aorta using an aortic arch (delivery) catheter. The distal end of the venous return catheter is usually placed in the right atrial appendage, while the proximal end of the catheter is attached to the tube feeding to a venous reservoir. The venous reservoir is placed at a lower level than the operating table to create a differential head pressure. This differential head pressure acts to siphon blood residing in the right atrium via the venous return catheter into the venous return reservoir.

During the open heart procedure, both the venous return catheter and aortic arch catheter are first introduced into the heart, and specifically the right atrium and inferior vena cava of the heart, and the aorta, respectively. The catheters are then clamped to inhibit blood flow therethrough. When the patient is ready to be placed on the extracorporeal circuit, the catheters are connected to inlet and outlet ends of the extracorporeal circuit, respectively, while simultaneously releasing the clamps.

Periodically, during the open heart procedure, the heart needs to be moved or adjusted by the surgeon. As the suction catheter and delivery catheter are already attached to the heart, there is a potential for these catheters to bend and kink, which can restrict blood flow therethrough and possibly create a dangerous and even life threatening situation. One prior art catheter which tends to avoid kinking is disclosed in U.S. Pat. No. 4,129,129 to Sarns. This catheter has an extremely thick tube body with a coil imbedded in the tube walls. Reinforcing the tube wall, however, significantly increases the outer diameter of the catheter. As such, the larger outer diameter requires a larger incision to be formed in the heart for introducing this large catheter, which tends to cause more trauma to the heart. Another disadvantage with this prior art catheter is that it can only be clamped in the non-reinforced area of the catheter which is provided at the proximal end of the catheter. This unreinforced section is in an inconvenient location for the surgeon, and restricts the surgeon from choosing the location of the clamp during the surgery.

There are three main areas of concern when performing the surgery in the conventional way. First, the kinking of the venous line, such as at the catheter tip, could potentially run the venous reservoir dry and allow air into the patient's circulation system. This introduction of air would be fatal. Secondly, the trauma on the heart created by a larger incision takes longer to heal and creates a larger scar. Finally, it is inconvenient for the surgeon to clamp only at the selected areas of the catheter.

There is a desire to provide a reinforced catheter that has a high inner to outer diameter ratio, a sufficient inner diameter and a small outer diameter which facilitates for smaller incision in the right atrium.

SUMMARY OF THE INVENTION

The present invention achieves technical advantages as a single lumen catheter including a semi-rigid support member extending within the catheter lumen. The support member preferably comprises a rod extending from the catheter proximal end to the distal end thereof. The rod is secured at the catheter distal end, but is free or not hinged at the proximal end of the catheter. A plurality of openings are provided circumferentially about the catheter distal end for draining blood from the right atrium of the heart into the catheter lumen. The rod positioned within the catheter lumen keeps the walls of the catheter tubing from collapsing when bent to extreme angles, thus facilitating continuous flow of blood therethrough. The inner diameter to outer diameter ratio of the catheter is high, providing a sufficient inner diameter while maintaining a small outer diameter which facilitates a smaller incision in the walls of the right atrium of the heart.

The venous return catheter of the present invention is particularly suitable for insertion into the right atrium and inferior vena cava of the heart. The single stage catheter comprises a flexible tube body having a lumen extending therethrough between a proximal end and a distal end. A rounded tip is secured to the distal end of the tube body and terminates the extension of the lumen. A plurality of openings are circumferentially positioned through the tube body proximate the distal end thereof. A relatively thin semi-rigid support member extends within the lumen and tends to prevent the flexible tube body from kinking or collapsing. The support member occupies about 5% of the lumen when viewed by cross section to prevent restriction of flow through the lumen. The support member has a smooth outer surface.

The support member is selectively or fixedly secured to a central portion of the tip at the tube body distal end, but is freely moveable with respect to the lumen at the tube body proximal end. Preferably, the support member has a circular cross section, but may also have an elliptical cross section or other suitable geometric configuration which facilitates clamping of the catheter to restrict fluid flow therethrough. In another embodiment, the support member may have radially extending support members engaging the catheter body walls. The support member secured at the catheter distal end is spaced away from the openings to avoid occlusion of the openings. Preferably, the plurality of openings longitudinally extend at least 4 inches from the tube body distal end towards the proximal end such that when placed in the heart, blood can be drawn via the openings from both the inferior vena cava and the right atrium of the heart. The rounded tip has a central recess facing the lumen and securely receives the support member therein. The rounded tip has a shouldered periphery. The tube body is securely received over this shoulder and provides a flush outer surface. In yet another embodiment, a linear support member could be integrally defined in the body wall to prevent kinking but facilitate clamping.

In an alternative preferred embodiment of the present invention, a two-stage catheter is provided wherein the tube body has a first diameter proximate the distal end, and a larger second diameter portion spaced from the distal end. The second diameter portion has an additional plurality of openings circumferentially positioned through the tube body. This two-stage catheter is ideally utilized in combination with an obturator tube to initially block flow of blood through the additional plurality of openings proximate the second diameter portion. This obturator tube is removed after the catheter is fully inserted into the heart.

The method of the present invention comprises by-passing blood flow from a heart during open heart surgery. The method comprises the steps of first introducing a venous return catheter into the right atrium of the heart via an incision formed in the atrium appendage wall. The catheter comprises a flexible tube body having a lumen extending between a proximal end and distal end thereof. A plurality of openings are circumferentially positioned through the tube body proximate the distal end. A semi-rigid support member extends within the lumen and tends to prevent the flexible tube from kinking. The support member is secured to a central portion of the tip at the tube body distal end and is freely movable with respect to the lumen at the tube body proximal end. The support member may have radially extending members to further prevent the catheter from kinking. The method of the present invention includes advancing the catheter into the right atrium until the distal tube body openings are positioned proximate the inferior vena cava of the heart. Next, blood is drained from the inferior vena cava via the tube openings and the tube body lumen. Preferably, the method of the present invention comprises the step of positioning the plurality of tube body openings to be proximate both the inferior vena cava and the right atrium of the heart to draw blood therefrom. Typically, the tube body is initially clamped to prevent fluid flow therethrough while inserting the tube body into the right atrium of the heart. The clamp is released as the extracorporal circuit is established.

In an alternative preferred method of the present invention, the catheter has a first diameter proximate the distal end, and a larger second diameter portion spaced from the distal end, the second diameter portion having an additional plurality of openings circumferentially positioned through the tube body. This alternative method comprises the additional step of positioning the additional plurality of openings to lie in the right atrium of the heart. An obturator tube is initially inserted into the lumen to initially block flow of blood through the additional plurality of openings above the second diameter portion. After the catheter is fully inserted into the inferior vena cava and the right atrium of the heart, the obturator tube is removed to permit fluid flow through both sets of openings.

BRIEF DESCRIPTION OF THE DRAWINGS

FIG. 1 is a sectional view of the human heart with a catheter of the present invention established in proper position for drawing blood from inferior vena cava and the right atrium of the heart;

FIG. 2 is a sectional side view of the single-stage catheter of the present invention including an integral semi-rigid support member extending through the lumen of the catheter to prevent kinking thereof;

FIG. 3 is a cross section of the catheter of FIG. 2 illustrating the circular cross section of the semi-rigid support member and the cross sectional area with respect to the lumen;

FIG. 4 is a cross section of a catheter according to an alternative preferred embodiment of the present invention wherein the semi-rigid support member has an elliptical cross section to further facilitate clamping of the catheter;

FIG. 5 illustrates the clamping of the catheter about the elliptical support member of FIG. 4;

FIG. 6 is a sectional side view of an alternative preferred embodiment having a semi-rigid support member extending within the lumen, the semi-rigid member having a plurality of radially extending support members arranged in a hub-spoke orientation;

FIG. 7 is a sectional side view taken along line 7—7 in FIG. 6 illustrating the hub-spoke arrangement of the semi-rigid support member;

FIG. 14 is a side view of a two-stage catheter according to a alternative preferred embodiment of the present invention also including an integral semi-rigid support member extending within the lumen to prevent kinking of the catheter during use; and FIG. 15 is a view of the catheter of FIG. 14 during installation with the obturator tube in place.

DETAILED DESCRIPTION OF THE PREFERRED EMBODIMENT OF THE PRESENT INVENTION

Figure 8:
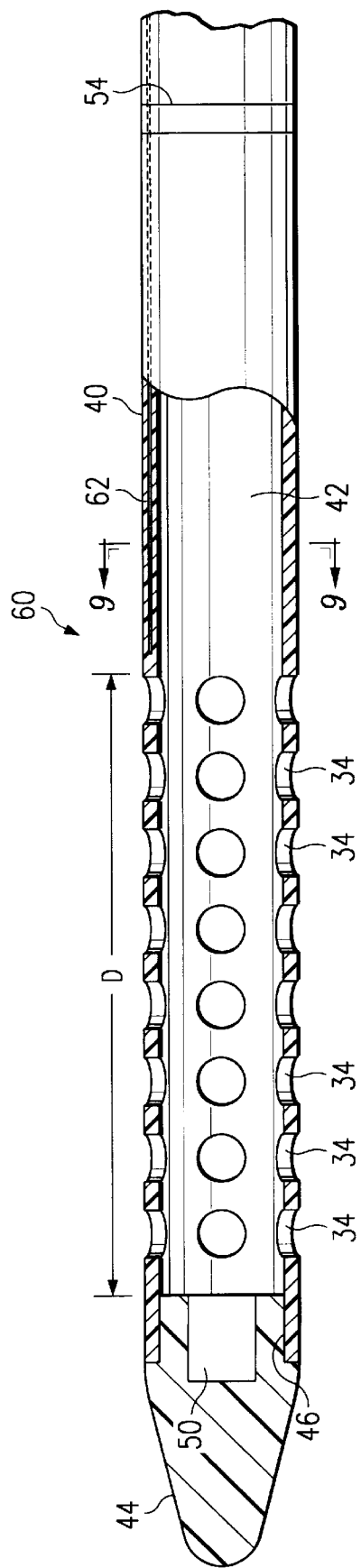
FIG. 8 is a sectional side view of another alternative preferred embodiment of the present invention comprising a linear semi-rigid support member integrally formed within the catheter wall to prevent kinking but allow clamping anywhere along the length of the catheter.

Referring now to FIG. 1, there is shown a section of a human heart 10 illustrating the right atrium 12 positioned above the inferior vena cava 14, the right ventricle 16, the superior vena cava 18 and the pulmonary artery 20. As illustrated in FIG. 1, the normally shaped right atrium has an atrial appendage generally shown at 22. This atrial appendage 22 is usually the most suitable location to form an incision for insertion of a venous catheter according to the preferred embodiment of the present invention.

Still referring to FIG. 1, a single stage venous return catheter 30 having a semi-rigid support member 32 is shown properly positioned in the heart. The support member 32 extends the length thereof to prevent kinking of the catheter during insertion, and use thereof. Properly used, catheter 30 is shown to be positioned with a plurality of openings 34 at a distal end thereof positioned in the inferior vena cava 14, with the most proximal openings 34 positioned in the right atrium 12 of the heart 10. Catheter 30 extends through the atrial appendage 22 via a small incision provided by the physician, as will be more fully described shortly in reference to FIGS. 10, 11, 12 and 13.

Referring now to FIG. 2, a sectional side view of the single-stage venous return catheter 30 is shown. Catheter 30 is comprised of a flexible tubular body 40 defining a lumen 42 extending from a proximal end to a distal end thereof. A solid, rounded nose or tip portion 44 has a shouldered periphery 46. Tubular body 40 is securely attached and positioned about the shoulder 46, as shown, and provides a flush outer surface. Rounded tip 44 terminates lumen 42 at a distal end thereof. Tip 44 is also seen to have a centrally located recess 50 securingly receiving the semi-rigid support member 32. Recess 50 is preferably filled with an adhesive or glue 52 to secure the distal end support member 32 into recess 50 and form a unitary member. Alternatively, support member 32 could be fused using RF welding to tip 44. By securing support member 32 in place at a central location of tip 44, support member 32 remains spaced from the plurality of circumferentially positioned openings 34 extending through the tube walls of body 40. Alternatively, member 32 could be selectively secured in a friction fit arrangement into recess 50, and thus be selectively detachable therefrom. The proximal end of support member 32, however, is free or not hinged with respect to lumen 42 to allow the body 40 to be freely bent, but without kinking.

Still referring to FIG. 2, the plurality of openings 34 are seen to be defined through the body walls a longitudinal distance "D" from tip 44 toward the proximal end of the catheter. Preferably, distance "D" is about 4 inches such that openings 34 are positioned both in the inferior vena cava 14 and the right atrium 12 when properly positioned, as shown in FIG. 1. Openings 34 facilitate blood to be drawn from the inferior vena cava 14 and the right atrium 12 when by-passing the heart and forming a portion of the extracorporal circuit (not shown). A reference mark 54, shown as a band, is marked around a mid section of the catheter 30. Band 54 designates the stopping point for insertion of lumen 30 into the right atrium 12, and assists the surgeon with proper positioning and insertion of catheter 30.

The semi-rigid support member 32 has a very small cross sectional area with respect to the diameter and cross section of lumen 42, as shown in FIG. 3 and FIG. 4, the member 32 preferably occupying about 5% of the lumen cross section to minimize restricting blood flow therethough. In the preferred embodiment of the present invention, the cross section of support member 32 has a circular cross section with a flush surface, but can also have an elliptical cross sec s shown in FIG. 4 if desired. The particular cross section of support member 32 facilitates clamping of the catheter 30 with a clamp as shown in FIG. 5 during use. This clamping inhibits the flow of fluid from openings 34 through lumen 42 until intended by the surgeon. Both the circular and elliptical cross section designs of the support member 32 have been found to be suitable. The particular cross section of member 32 is provided to be commensurate with the type of clamp utilized by the surgeon.

The semi-rigid support member 32 is preferably comprised of PVC, or formed of other suitable plastics, or a malleable metal. The tip 44 is preferably formed of a ridged plastic, such as polyvinyl chloride. The tubular body 40 is formed of a material having sufficiently flexing qualities, such as PVC or silicone.

In the preferred embodiment of the present invention, catheter body 40 has an outer diameter of 0.550 inches, and an inner diameter of 0.460 inches, thus providing a wall thickness of 0.045 inches. The diameter of support member 32 is 0.100 inches, and thus occupies less than 5% of the area of lumen 42. The diameter of openings 34 is approximately 0.200 inches although limitation to these dimensions is not to be inferred in the present invention.

Referring now to FIG. 6, there is shown generally at 56 a sectional side view of a single-stage venous return catheter according to an alternative preferred embodiment of the present invention. Catheter 56 is similar to the catheter 30 shown in FIG. 2 wherein like numerals refer to like elements. The semi-rigid support member 32 has been modified to include a plurality of integral radially extending support members 57 each which extends to a respective flange 58. Flanges 58 extend towards, and preferably but not necessarily engage, the inner lumen walls of body 40. Radial members 57 provide additional catheter support along the length thereof and prevent kinking while minimizing obstruction of fluid flow through lumen 42. Six radial support members 57 are provided at uniform intervals along the length of the semi-rigid support member 32 to facilitate flexing of the catheter, as shown in FIG. 6, although more or less members 57 could be used if desired. The uniform spacing of the radial members 57 in the longitudinal direction is shown in FIG. 7. The flanges 58 extend in the longitudinal direction with respect to lumen 42 to minimize restriction of fluid flow therethrough. While a single stage catheter is shown, it is to be understood a two-stage catheter could also implement the modified support member 32 with radial support members 57 if desired.

Referring now to FIG. 8, there is shown generally at 60 a sectional side view of a single-stage venous return catheter according to yet another alternative embodiment of the present invention. Catheter 60 is similar to catheter 30 shown in FIG. 2, wherein like numerals refer to like elements. In this embodiment, a linear semi-rigid support member 62 is integrally formed in the catheter walls of body 14 along the length of the catheter. Member 62 is linear to provide reinforcement and prevent kinking of the catheter body 40, but allows clamping of catheter 62 anywhere along the length of body 40. Linear support member 62 is preferably comprised of a semi-rigid molded plastic material, but may also be comprised of a metal material if desired.

Figure 9:
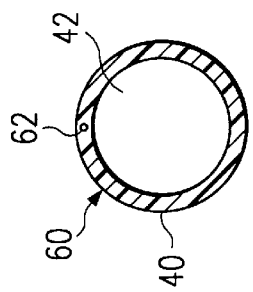
FIG. 9 is a sectional side view taken along line 9—9 in FIG. 8 illustrating the semi-rigid member in the catheter wall.

Member 62 is formed within the catheter walls when body 40 is formed. The lumen 42 is unobstructed and facilitates good fluid flow therethrough. In addition, the diameter of support member 62 is very small being about 0.040 inches, as shown in FIG. 9, allowing a reduced outer diameter of body 40 being 0.550 inches and a sufficient inner diameter being 0.440 inches, as discussed in reference to the catheter 30 shown in FIG. 2. The linear semi-rigid member 62 could be integrally formed in the body walls of a two-stage venous return catheter as well, if desired. The semi-rigid member 62 is shown as extending from proximate the openings 34 toward the proximal end of the catheter, but could also extend distally and closely proximate the tip 44, along the openings 34, if desired.

METHOD OF USE

Figure 10:
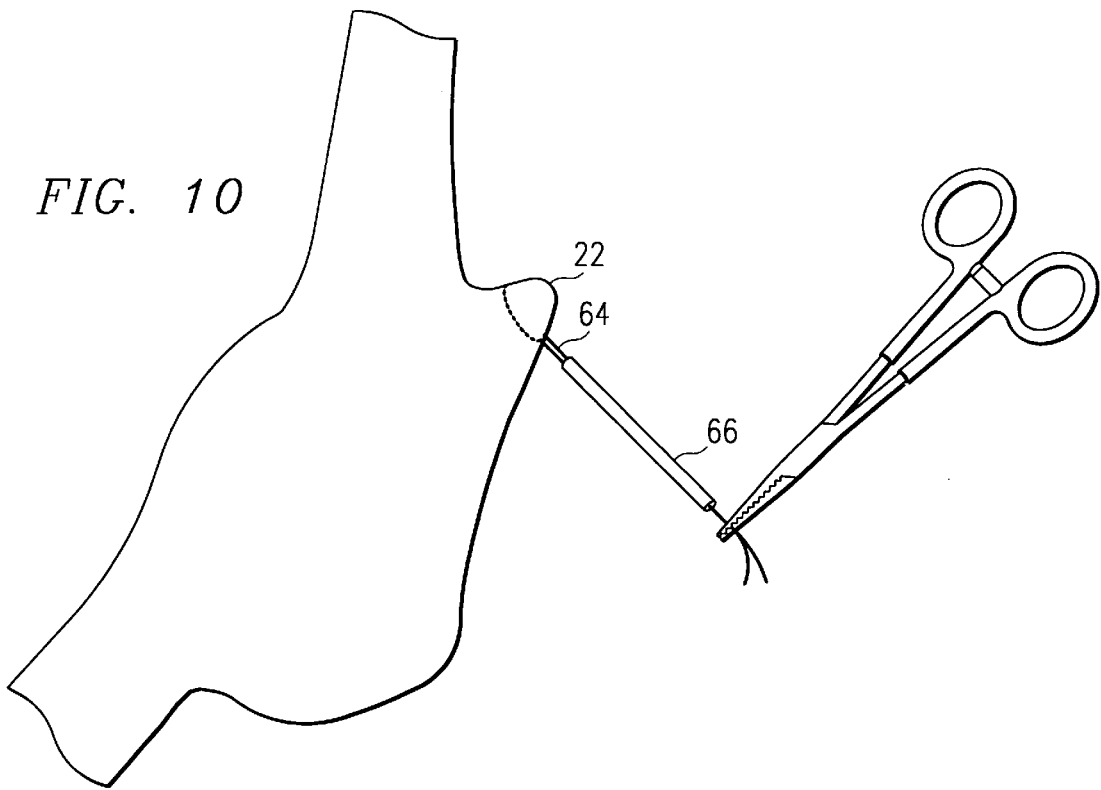
FIGS. 10, 11, 12 and 13 illustrate the sequence of installing the single-stage catheter according to the preferred method of the present invention.
Figure 11:
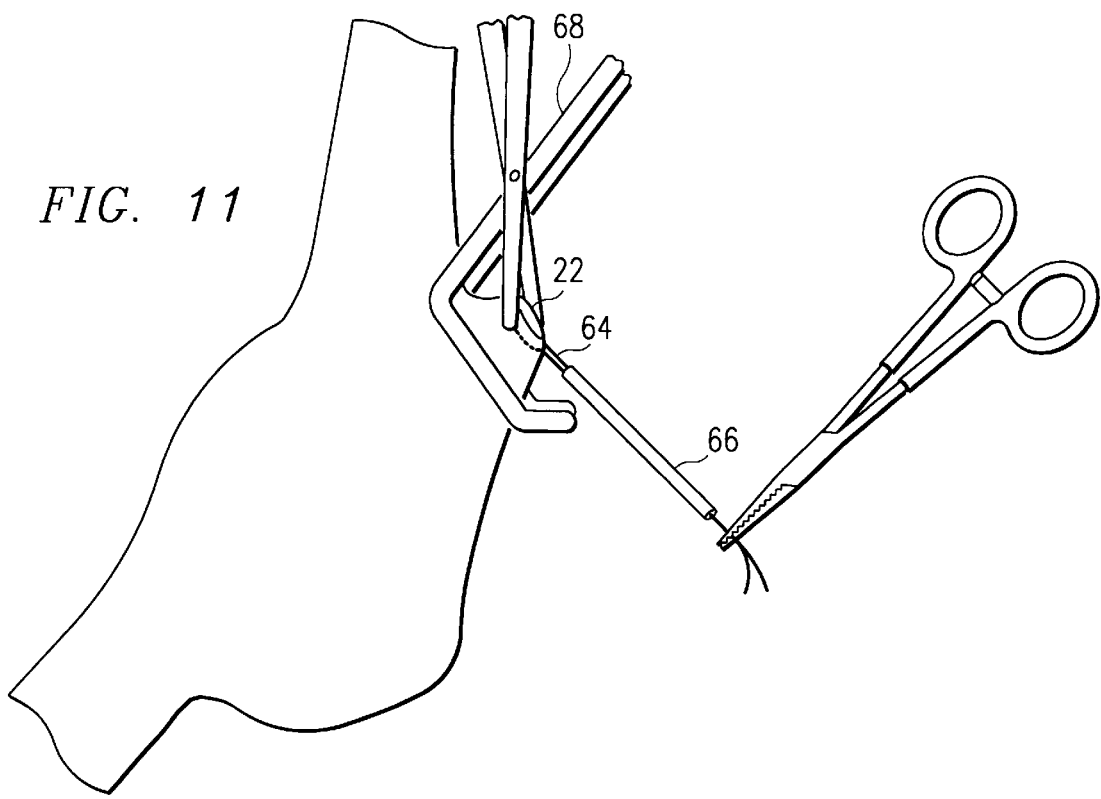
Figure 12:
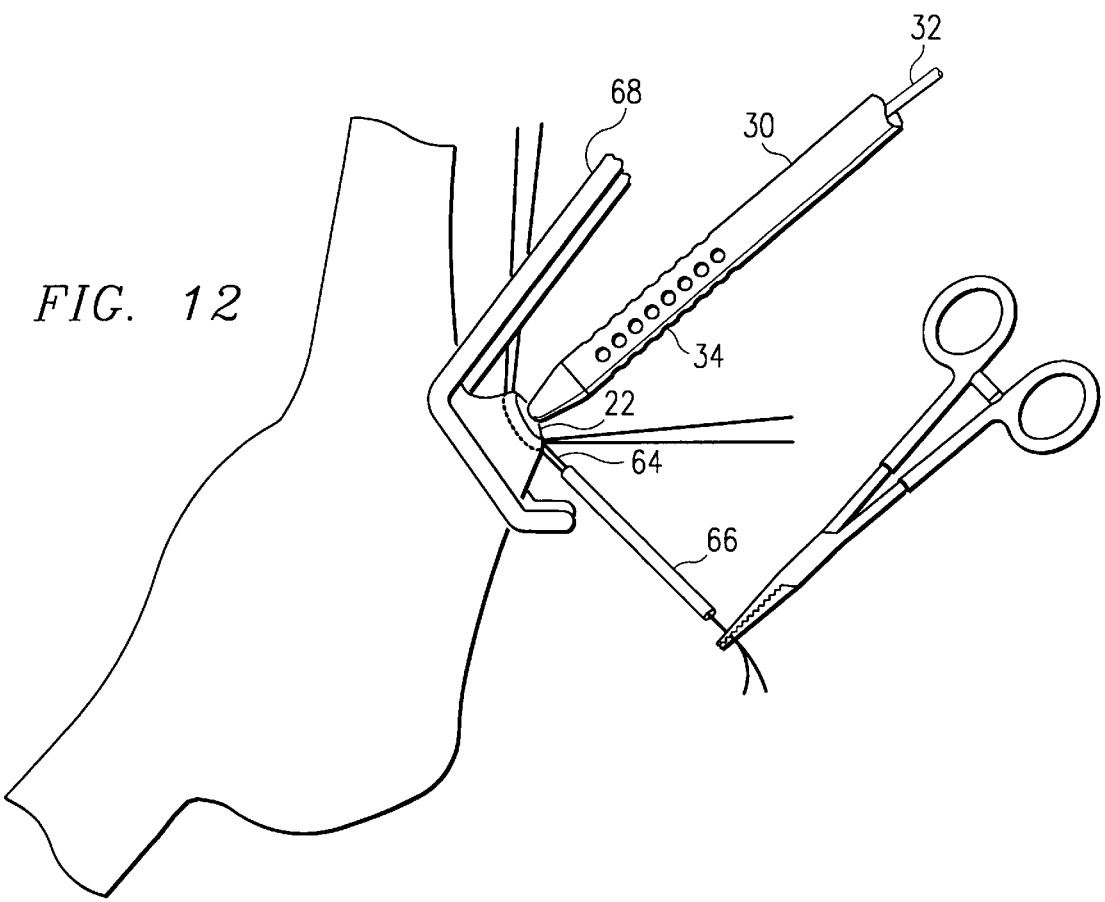
Figure 13:
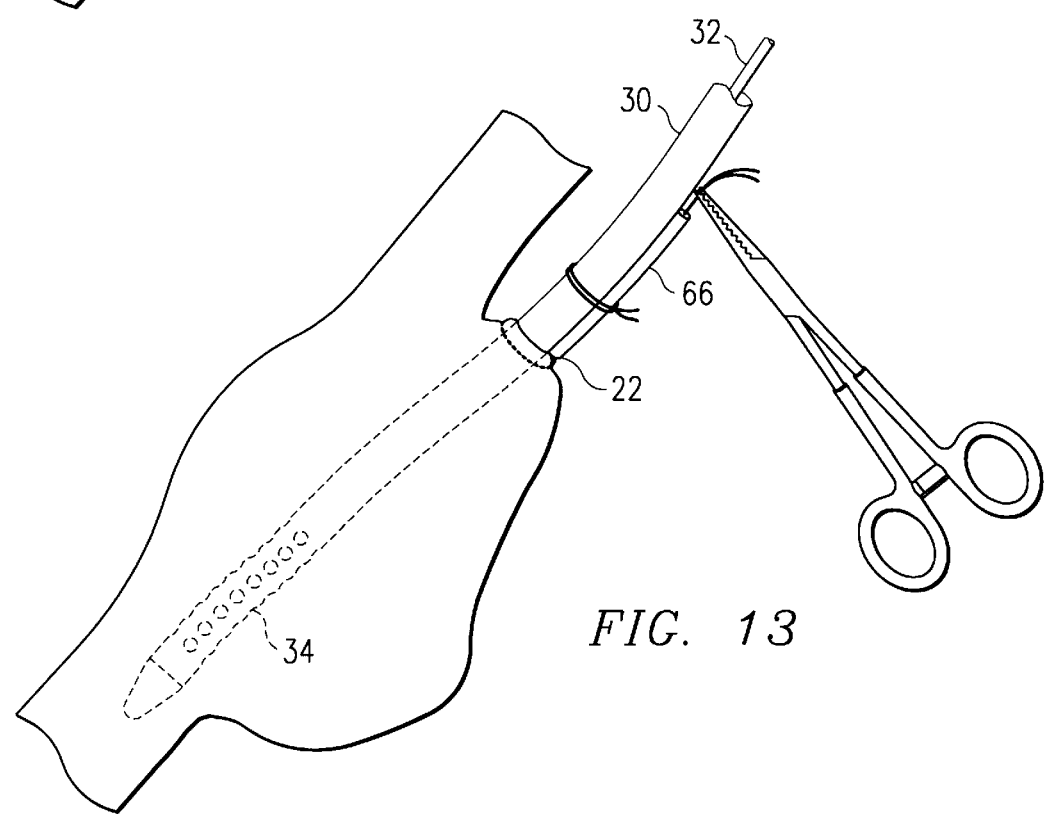

Referring now to FIGS. 10–13, the use of either catheter 30, 56 and 60 according to the preferred embodiments of the present invention will now be discussed in considerable detail. Referring first to FIG. 10, a purse-string suture 64 is placed around the right atrial appendage 22 and drawn through a rubber ligature tube 66. Referring to FIG. 11, a vascular clamp 68 is then used to isolate the purse string suture 64 while the end of the distal appendage 22 is amputated, or an incision is made in the middle of the purse string suture 64. The atriotomy is then opened with clamps or traction sutures and the tip 44 of the catheter 30, 56 or 60 is inserted, as shown in FIG. 12. The catheter is further inserted into the atrium toward the inferior vena cava until the tip 44 of the catheter is positioned in the inferior vena cava. The catheter 30 is pushed into the right atrium 12 until the mark 54 of the catheter is positioned proximate the incision of the appendage 22. The plurality of openings 34 are positioned within both the inferior vena cava 14 and the right atrium 12 to permit the collection of blood from the coronary sinus and venous return from the inferior vena cava 14 and the superior vena cava 18, as shown in FIG. 1. The purse string suture 64 is then pulled tight around the tubular body 40, as shown in FIG. 13. The occluding vascular clamp (shown in FIG. 5) is released to connect the heart to the extracorporeal circuit. When the operation is completed, the catheter is removed and the purse string suture is tied.

Referring now to FIG. 14 there is shown a two-stage catheter at 70 that is similar to the single stage catheter 30, wherein like numerals refer to like elements, but is distinguished as having a second diameter portion 72 spaced from the distal tip 44 having an increased diameter from that portion 76 about the first plurality of openings 34. A second plurality of openings 74 are shown to be circumferentially defined through the walls of catheter body at portion 72, the spacing between the sets of openings being about one inch.

Referring to FIG. 15, there is shown an obturator tube 80 being utilized to provide for more time for catheter 70 to be inserted to reduce blood loss. As shown in FIG. 15, as catheter 70 is initially inserted to the appendage 22, the obturator tube 80 is positioned in lumen 42 past the second set of openings 74 and closely proximate the first of openings 34, but short thereof to allow fluid communication through the first set of openings 34 into tube 80. The initial blood flow will proceed through the first set of openings 34 proximate the distal end of the catheter 70 and into the tube 80, with the tube 80 temporarily blocking the second set of openings 74. After catheter 70 is fully inserted into the right atrium 12, the first set of openings 34 will be positioned proximate the inferior vena cava 14, with the second set of openings 74 being positioned in the right atrium 12. The first set of openings 34 draw blood from the inferior vena cava 14, and a second set of openings 74 draw blood from the right atrium 12. As shown, the semi-rigid support member 32 extends the length of catheter 70 from the distal tip 44 to prevent kinking of the catheter during insertion and use. Similar to catheter 30, the semi-rigid 32 is secured at a central portion of tip 44 and away from the openings 34. In addition, a lumen body shoulder 78 maintains support member 32 to be positioned relatively free of the openings 74 as well to avoid any significant interference of blood flow from the openings 74 into the lumen.

In summary, a single stage and two stage catheter is shown to include a semi-rigid support member 32 extending within a lumen 42 thereof to provide structural support which avoids kinking of the catheter during installation and use. The use of the integral support member in the lumen, or a linear support member in the catheter wall, allows the catheter to have a smaller outer diameter to be implemented, wherein the inner to outer diameter ratio of the catheter is very high, and the inner diameter is sufficient for necessary blood flow. The present invention eliminates the need for any coiled reinforcement in the catheter walls, thereby allowing a catheter with a sufficiently small outer diameter to be utilized, thus requiring a smaller incision in the right atrium which is less traumatic. Since the support member is provided in the lumen of the catheter, or is linearly defined in the body wall, and the catheter body is flexible, the clamp can be placed by the surgeon anywhere the surgeon chooses along the length of the catheter to shut off the flow within the catheter.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A venous return catheter for insertion into the right atrium and inferior vena cava of the heart, comprising:
    a flexible tube body having a lumen extending therethrough between a proximal end and a distal end;
    a tip secured to said distal end of said tube body;
    at least one opening positioned through said tube body proximate said distal end; and
    a semi-rigid support member extending within said lumen and connected to said tip tending to prevent said flexible tube from kinking, said support member having a plurality of radially extending support extensions, wherein said support extensions engage said tube body and comprise radially extending fingers having flanged tips.

2. The catheter as specified in claim 1 wherein said support member is secured to a central portion of said tip at said tube body distal end and freely movable with respect to said lumen at said tube body proximal end.

3. The catheter as specified in claim 1 wherein said support member is selectively secured to and detachable from said tip.

4. The catheter as specified in claim 1 wherein said support member is fixedly secured to said tip.

5. The catheter as specified in claim 1 wherein said support member has a circular cross section.

6. The catheter as specified in claim 1 wherein said support member is secured away from said opening to avoid occlusion of said opening.

7. The catheter as specified in claim 1 comprising a plurality of said openings circumferentially positioned through said tube body proximate said distal end.

8. The catheter as specified in claim 7 wherein said plurality of openings extend at least 4 inches from said tube body distal and towards said proximate end.

9. The catheter as specified in claim 1 wherein said tip has a central recess facing said lumen and securingly receiving said support member.

10. The catheter as specified in claim 9 wherein said tip has a shouldered periphery with said tube body being securingly received over said shoulder.

11. A venous return catheter for insertion into the right atrium and inferior vena cava of a heart, comprising;
    a flexible tube body having a lumen defining a lumen wall and extending therethrough between a proximal end and a distal end;
    a tip secured to said distal end of said tube body;
    at least one opening positioned through said tube body proximate said distal end; and
    a semi-rigid support member extending within said lumen tending to prevent said flexible tube from kinking, said support member being spaced from said lumen wall to permit fluid flow therethrough, said support member has a plurality of radially extending support extensions engaging said tube body and comprising radially extending fingers having flanged tips, wherein said support member has a non-circular cross-section.

12. The catheter as specified in claim 11 wherein said support member is connected to said tip.

13. A venous return catheter for insertion into the right atrium and inferior vena cava of a heart, comprising;
    a flexible tube body having a lumen defining a lumen wall and extending therethrough between a proximal end and a distal end;
    a tip secured to said distal end of said tube body;
    at least one opening positioned through said tube body proximate said distal end; and
    a semi-rigid support member extending within said lumen tending to prevent said flexible tube from kinking, said support member being spaced from said lumen wall to permit fluid flow therethrough, said support member having a non-circular cross section, wherein said support member has an elliptical said cross section.

* * * * *